United States Patent [19]

Chevallier

[11] Patent Number: 4,872,868
[45] Date of Patent: Oct. 10, 1989

[54] COLLECTING BAG FOR MAKING QUICK MEDICAL ANALYSES

[76] Inventor: François Chevallier, 10 boulevard Périer, 13008 Marseille, France

[21] Appl. No.: 252,036

[22] Filed: Sep. 28, 1988

Related U.S. Application Data

[63] Continuation of Ser. No. 140, Jan. 2, 1987, abandoned.

[30] Foreign Application Priority Data

Jan. 3, 1986 [FR] France ................ 86 00033

[51] Int. Cl.4 ............................................. A61M 1/00
[52] U.S. Cl. .................................... 604/327; 128/767; 128/771; 383/41; 604/332
[58] Field of Search ................ 604/317, 318, 322–327, 604/332–355, 277, 404, 408, 409, 410; 128/760–762, 767, 768, 771; 383/38–41, 47, 66, 907; 206/305, 306

[56] References Cited

U.S. PATENT DOCUMENTS

| 3,186,409 | 6/1965 | Bartz | 383/66 |
| 3,618,606 | 11/1971 | Brown et al. | 604/334 |
| 3,762,399 | 10/1973 | Riedell | 128/767 |
| 3,831,453 | 8/1974 | McWhorter | 128/771 |
| 4,445,898 | 5/1984 | Jensen | 604/332 |
| 4,473,530 | 9/1984 | Villa-Real | 128/771 |

FOREIGN PATENT DOCUMENTS

| 1007533 | 3/1977 | Canada | 128/771 |
| 0042973 | 1/1982 | European Pat. Off. | 604/334 |
| 0225337 | 7/1985 | Fed. Rep. of Germany | 604/318 |
| 3304312 | 6/1984 | German Democratic Rep. | 604/332 |
| 8404036 | 10/1984 | PCT Int'l Appl. | 604/317 |

Primary Examiner—C. Fred Rosenbaum
Assistant Examiner—Mario Costantino
Attorney, Agent, or Firm—Wolf, Greenfield & Sacks

[57] ABSTRACT

The invention relates to a collecting bag for making quick medical analyses allowing the making of a diagnosis or monitoring the evolution of the state of health of a patient comprising a pocket characterized in that it is provided with an additional orifice (14) allowing the insertion of a product or instrument or the sampling of the contents of the bag (10). The present invention finds its main application in the field of medical analysis.

10 Claims, 1 Drawing Sheet

COLLECTING BAG FOR MAKING QUICK MEDICAL ANALYSES

This application is a continuation of application Ser. No. 000140, filed Jan. 2, 1987, now abandoned.

BACKGROUND OF THE INVENTION

The present invention relates to a collecting bag for making quick medical analyses permitting making a diagnosis or monitoring the evolution of the state of health of a patient.

Various types of collecting bags are already known for collecting stools, urine or other human secretions. What is intended here is to collect, for example, stools after a colostomy or ileostomy, or also the urine either of infants or of incontinent adults. The bags already in existence also permit collecting secretions in the case of fistulae or during post-operational care. All the existing types of bags, open or closed, have a fixing system for ensuring the fixing of the bag to the body. This fixing system is generally an adhesive or a skin protector, but may also be a belt or any other fixing system.

Types of apparatus are already known made up of two parts, such as a skin protector fixed to the body and a collecting bag subsequently fitted to the skin protector.

None of these types of collecting bags allow an instantaneous and direct biological ayalysis. The materials collected in the bag are of necessity taken from the bag and then sent to the laboratory for the desired biological analysis.

In addition, the taking of materials from said bags fitted with an outflow or an opening is not always easy. Finally, it is impossible for the user to carry out a direct and instantaneous monitoring of the evolution of his or her state of health without undergoing a biological analysis in the laboratory.

SUMMARY OF THE INVENTION

The present invention has for its object to avoid such drawbacks and aims at providing a collecting bag allowing the performing of quick medical analyses permitting making a diagnosis or monitoring the state of health of the user without the need of a systematic recourse to a laboratory analysis.

For the purpose the invention relates to a collecting bag of the type consisting of a closed flexible envelope fitted with an opening for the passing through of matter such as stools, urine, secretions or others originating from the individual, a bag characterized in that it is provided with an additional orifice allowing the insertion of a product or an instrument for the sampling of the contents of the bag.

Such a collecting bag allows the user to perform a quick medical analysis enabling a diagnosis to be made or permitting the monitoring of the evolution of his or her state of health. Indeed, this bag allows, in a great number of situations, the user himself or herself, or anyone attending to him or her, to effect a very useful supervision for prevention in medical terms. The additional orifice with which the bag is provided allows the insertion thereinto of a biological reagent revealing the constituent looked for. The additional orifice allows the insertion of any type of reagent, be it liquid, in powder or granular form, or again as testing strips.

Thus, the patient or the person in attendance is able to detect, for example, the presence of blood in stools or urine. Said bag also allows the disclosure of an excess or lack of glucose. The bag also allows showing up the insufficiency of some electrolytes. It is obviously possible to imagine other additional forms of medical analysis able to be performed by an individual or a person in attendance.

According to another characteristic of the invention the bag has a provision for the fitting of an instrument or product coming in contact with the contents of the bag.

According to another characteristic of the invention the additional orifice is a slit for accessing to the inside of the bag, said slit constituting the inlet for the provision.

According to another characteristic of the invention the bag has a cut-out portion defining a foldable tongue which seals the access slit in folded back position over the slit.

According to another characteristic of the invention the free end of the tongue is provided with a fixing member such as an adhesive securing the tongue in the folded back position for sealing the slit and ensuring the self-tightness of the bag.

Finally, according to a further characteristic of the invention the provision is obtained by welding points of the walls of the bag along at least one edge of the latter.

The object of this provision is to keep the reagent within a delimited and specific area of the collecting bag so as to be able to monitor precisely the area where the reaction is to take place.

The present invention will be better understood on the basis of an embodiment, on the one hand, of a standard collecting bag of the state of the art and, on the other hand, of a collecting bag according to the invention, both represented diagrammatically as non-limitative examples in the drawings:

DESCRIPTION OF THE PREFERRED EMBODIMENTS

Figure 1:
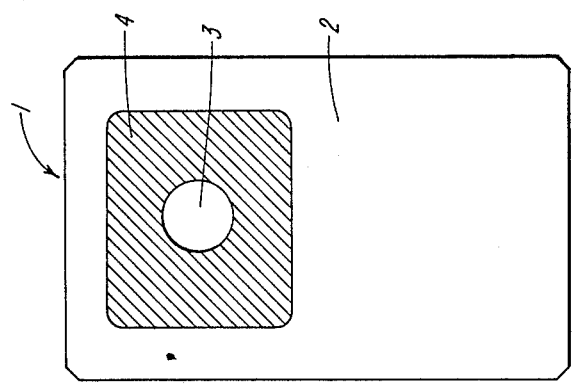
FIG. 1 is a top view of a collecting bag of the state of the art.

According to FIG. 1 the collecting bag 1 of the state of the art consists in an envelope 2 provided with an orifice 3 and an adhesive or a skin protector 4.

According to this type of bag it is absolutely necessary to take a sample in the laboratory for a medical analysis of the contents allowing a diagnosis to be made or permitting the monitoring of the state of health of a patient. It is therefore impossible for the individual or an attending person to perform self-monitoring.

Figure 2:
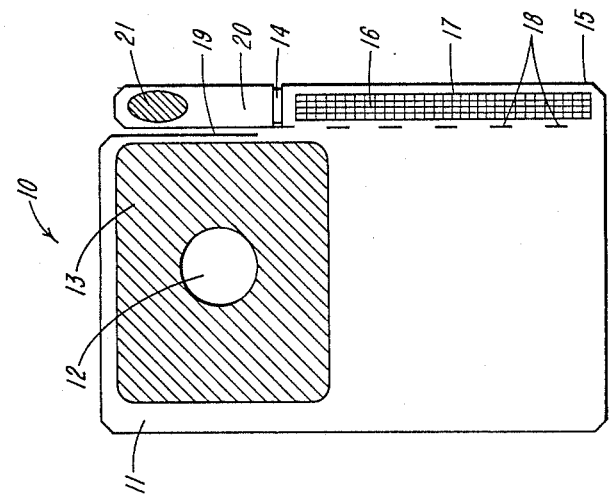
FIG. 2 is a top view of a collecting bag according to the invention.

According to FIG. 2 the collecting bag 10 according to the present invention allows a quick medical analysis to be performed by the patient himself or herself or by an attendant so as to make a diagnosis or perform a monitoring of the evolution of the state of health.

The collecting bag 10 is constituted by an envelope 11 provided by an orifice 12 allowing the passage of matter to be collected. The orifice 12 is surrounded by an adhesive or a skin protector 13.

The collecting bag 10 has in addition an additional orifice 14 allowing the insertion of a product or an instrument or permitting the taking of a sample of the contents of the bag 10.

The bag 10 has close to one of its edges 15 an additional chamber 16 allowing the insertion of an instrument such as a test strip 17 or a product coming in contact with the contents of the bag. The additional chamber 16 is obtained by weld points 18 allowing the fixing of the walls of the envelope 11 in the vicinity of the edge 15 to obtain the additional chamber 16.

The orifice 14 is constituted by a slit for access to the inside of the bag 10. The orifice 14 also constitutes the inlet of the additional chamber 16. The additional chamber is not necessarily in the vicinity of the edge. The figure shown proposes a additional chamber situated near an edge of the bag and to which access is gained by a slit. The additional chamber may be situated elsewhere on the bag and the access orifice is not necessarily a slit.

The collecting bag 10 has a cut-out portion 19 defining a tongue 20. This can fold back on itself to seal the additional orifice 14. The tongue 20 has fitted with a fixing member such as an adhesive 21 holding the tongue 20 in folded back position sealing the additional orifice 14 and simultaneously sealing the bag.

The collecting bag 10 may be used for various types of medical care such as colostomy, ileostomy, urostomy, drains, urine collection in pediatrics or for incontinent adults. It is possible to envisage other possibilities without departing from the scope of the invention.

The additional chamber 16 made by welding points on the walls of the envelope 11 allows the insertion of various types of reagents in liquid, powder, granular or test strip form. The additional chamber 16 allows both the insertion of a reagent and the placing of said reagent in contact with the contents of the bag.

The tongue 20 and the adhesive 21, in the folded back position sealing the additional orifice 14, prevent the contents of the bag 10 from leaking and ensure the seal-tightness of the latter.

It is possible to imagine the insertion of various devices into the additional chamber such as, e.g., degassing filters for colostomy bags.

I claim:

1. A collection bag for performing quick medical analysis allowing the making of a diagnosis or the monitoring of the evolution of the state of health of a patient comprising,
    a collection chamber defined by a closed, flexible envelope,
    a first orifice for allowing for passage into the collection chamber of matter such as stools, urine, secretions or other material originating from the patient,
    a second chamber defined by a weld point of the walls of the bag along at least one edge of the bag, the second chamber in fluid communication with the collection chamber, and
    a second orifice constructed and arranged both to allow insertion of a product or an instrument into the second chamber and to allow for sampling the contents of the bag, the second orifice comprising a slit for access inside the bag, the slit constituting the inlet of the second chamber.

2. A collection bag for performing quick medical analysis allowing the making of a diagnosis or the monitoring of the evolution of the state of health of a patient comprising,
    a collection chamber defined by a closed, flexible envelope,
    a first orifice for allowing for passage into the collection chamber of matter such as stools, urine, secretions or other material originating from the patient,
    a second chamber defined by a weld point of the walls of the bag along at least one edge of the bag, the second chamber in fluid communication with the collection chamber,
    a second orifice constructed and arranged both to allow insertion of a product or an instrument into the second chamber and to allow for sampling the contents of the bag, and
    a cut-out portion defining a foldable tongue which seals the second orifice in a folded-back position over the orifice.

3. A collection bag as claimed in claim 2, wherein the free end of the tongue is fitted with a fixing member such as an adhesive holding the tongue in folded-back position sealing the second orifice and thus sealing the bag.

4. A collection bag for performing quick medical analysis allowing the making of a diagnosis or the monitoring of the evolution of the state of health of a patient comprising,
    a flexible bag defining a collection chamber, an opening in the bag communicating directly with the collection chamber for allowing passage into the collection chamber of matter such as stools, urine, secretions or other material originating from the patient,
    means associated with the bag forming a discrete second chamber having a smaller volume than the collector chamber and in fluid communication with the collection chamber, the second chamber-forming means constructed and arranged to removably receive and hold in place an instrument,
    a second opening in the bag in fluid communication with both chambers, the second opening constructed and arranged to allow an instrument to be inserted therethrough and into the second chamber, and
    means attached to the bag for resealably closing the second opening.

5. A collection bag as claimed in claim 4 wherein the second chamber-forming means comprises weld lines in the bag.

6. A collection bag as claimed in claim 5 wherein the closing means is a foldable tongue.

7. A collection bag as claimed in claim 6 wherein the tongue is a cut-out portion of the material from which the bag is made.

8. A collection bag as claimed in claim 5 wherein the second opening is a slit in the bag.

9. A collection bag as claimed in claim 7 wherein the second opening is a slit in the bag.

10. A collection bag as claimed in claim 6 wherein the second chamber is a longitudinal chamber formed along one side of the bag and the foldable tongue is disposed along the same axis as the longitudinal chamber, the tongue being cut-out of the material from which the bag is made.

* * * * *